United States Patent [19]

Wang et al.

[11] Patent Number: 5,008,199
[45] Date of Patent: Apr. 16, 1991

[54] **HYBRIDOMA CELL LINE AND MONOCLONAL ANTIBODIES TO *TREPONEMA DENTICOLA* ATCC 33520**

[75] Inventors: Dou-Mei Wang, Randolph; Linda D. Sturdivant, East Orange; Thomas A. Biemer, Mine Hill, all of N.J.; Ronald Mink, Wilbraham, Mass.

[73] Assignee: Warner-Lambert Company, Morris Plains, N.J.

[21] Appl. No.: 123,014

[22] Filed: Nov. 19, 1987

[51] Int. Cl.$^5$ .............................................. C12N 5/00
[52] U.S. Cl. ............................... 435/240.27; 530/387; 935/104
[58] Field of Search .................. 435/240.27, 68, 104; 530/387

[56] References Cited

PUBLICATIONS

Simonson et al., 64th General Session of the International Assoc. for Dental Research, The Hague, Netherlands, Jun. 26–28, 1986, J. Dent. Res. 65, 1986.

Tall et al., 86th Annual Meeting of the ASM, Wash., D.C., Mar. 23–28, 1986, Abst. Annu. Meeting Am. Soc. Micro. 86, 1986.

Goding, J. Immunol. Methods 39, 1980, pp. 285–308.

*Primary Examiner*—Christine Nucker
*Assistant Examiner*—Karen I. Krupen
*Attorney, Agent, or Firm*—Daniel A. Scola, Jr.; Craig M. Bell

[57] ABSTRACT

Monoclonal antibody to *Treponema denticola* ATCC 33520 and a continuous cell line for its production is disclosed. These antibodies are particularly useful in immunoassays for detecting the presence of these microorganisms in the oral cavity.

5 Claims, No Drawings

HYBRIDOMA CELL LINE AND MONOCLONAL ANTIBODIES TO *TREPONEMA DENTICOLA* ATCC 33520

FIELD OF THE INVENTION

This invention relates to the production of a continuous hybridoma cell line capable of producing monoclonal antibodies to Treponema species ATCC #33520 deposited with ATCC, Rockville, Maryland under their procedure for complying with deposits of cultures for patent purposes.

BACKGROUND OF THE INVENTION

In 1975 Kohler and Milstein demonstrated that individual clones of normal antibody-secreting cells could be fused with myeloma cells to produce a continuous cell line or culture which secreted monoclonal antibody to sheep red blood cells. *Nature.* Vol. 256,495 (1975). Since then numerous publications and patents have appeared describing the production of monoclonal antibodies to a variety of antigens and haptens. See, for example, "Monoclonal Antibodies: A Powerful New Tool in Biology and Medicine," Yelton, D. E. and Schaff, M. D., *Ann. Rev. Biochem.* 50:657-80, 1981; "Antibody Production by Hybridomas," Goding, James W., *Journal of Immunological Methods.* 39:285-308 (1980).

In monoclonal antibody production, each cell synthesizes a homogeneous or monoclonal immunoglobulin that represents one of the many antibodies produced by the immunized animal. For example, U.S. Pat. No. 4,521,540 discloses the production of hybridoma cell lines which produce monoclonal antibodies to theophylline. PCT Application No. GB85/00465 disclosed monoclonal antibodies to the genus Treponema. In particular, the monoclonal antibodies disclosed in this reference are specific to *Treponema pallidum* I, II and III; *Treponema phagedenis; Treponema macrodentium* or *T. dentium: Treponema pertenue; Treponema cuniculi; Treponema refrigens; Treponema macrodenin:* and *Treponema mucosum.* Additionally this reference discloses a monoclonal antibody cross-reactive with an antigen for each species of the genus Treponema.

Presently, diagnostic test kits using monoclonal antibodies have proved to be very useful due to their specificity and ability to produce reasonably accurate results. No such test kit is presently available, however, which accurately identifies the presence of oral disease, i.e., periodontitis, gingivitis and other diseases which evidence inflammation and subsequent loss of bone and gum tissue in the mouth. One reason for this is the difficulty in determining which organisms are the best indicators or causes of oral disease. Efforts in the development of a semi-quantitative diagnostic test useful for the detection of periodontal disease have focused on forming reagents to detect certain species of Treponema. A number of different bacterial organisms have been implicated in the disease process, but recently certain species of Treponema, a type of spirochete organism, have been shown to increase significantly in total microbial population as the disease progresses. (See *Journal of Periodontology* 53:550-556; 36:177-187; 38:379-386; 46:10-26; and *Journal of Clinical Periodontology* 8:122-138.) This organism is believed to play a major role in the oral disease process.

The human mouth provides a media rich in protein and amino acids, as well as other organic acids and inorganic substrates necessary for the growth and support of organisms. This complex environment necessitates development of reagents which are specific for and react only to the organisms of interest. Antibodies have the ability to recognize and bind specifically to the organisms used to generate them. For this reason, Treponema reactive antibodies were chosen as the reagents to be used in the development of the inventive assay and diagnostic tests which are useful in diagnostic test kits. This invention describes the formation of a polyclonal murine hybridoma cell line, subsequent cloning to obtain a monoclonal antibody secreting cell line and the reactivities of these novel antibodies. A method of using these monoclonal antibodies to diagnose the presence of the Treponema species described.

SUMMARY OF THE INVENTION

Monoclonal antibodies have been developed that permit the quantitative and qualitative detection of oral strains of the spirochete species Treponema. A Hybridoma cell line capable of producing IgG to *Treponema denticola* ATCC 33520 was formed by fusing a non-secreting mouse myeloma cell with a spleen cell from a mouse immunized with cell fragments of the spirochete *Treponema denticola* ATCC 33520. Thus, this invention comprises the hybridoma cell line formed and the monoclonal antibodies produced in vitro by these hybridomas. The invention, because of the specific reactivity of the antibodies, is useful for the detection of this particular Treponema species in the presence of other organisms normally found in the mouth. This particular Treponema species is commonly found in the mouth along with a host of other microorganisms and it is the advantage of the instant invention that the antibodies produced by the inventive cell line are not cross-reactive with these other organisms, but are specific to *Treponema denticola* ATCC 33520. Thus, the antibodies are also potentially useful in diagnostic test kits for assaying oral disease in which Treponema spirochetes are implicated.

DETAILED DESCRIPTION AND PREFERRED EMBODIMENTS

The bacterial strain used in this invention, *Treponema denticola* ATCC 33520 was obtained from the American Type Culture Collection, Rockville, Maryland. The Treponema was cultured under anaerobic conditions at 37° C. in synthetic media comprising, in grams/liter, 1.5 trypticase, 0.5 yeast extract, 0.25 NaCl, 0.05 sodium thioglycollate, 0.1 1-cysteine-HCl-$H_2O$, 0.3 pectin and 0.0001 resazurin. These ingredients were admixed in a flask, stirred and boiled until the media became anaerobic, as evidenced by media color change. This generally occurs within a minute after boiling begins. The resultant mixture was autoclaved at 121° C. for about 15 to 30 minutes. Pectin medium was further supplemented aseptically after autoclaving with (per 100 ml) 2.67 ml of sterile 7.5% (w/v) $NaHCO_3$ and 3.0 ml of sterile TPP/VFA solution (0.03%/0.05%).

Preparation of Treponema Antigens 33520

The above-mentioned culture was grown to a density of approximately $10^6$ cells/ml. Approximately 200 ml of the culture was taken, centrifuged at 10,000×g, 20 minutes, and resuspended to an absorbance (660 nm) of 1.50 in 0.1 M Tris buffer, pH 6.8, under anaerobic conditions. The cells were once again centrifuged and washed three times in fresh Tris buffer, and diluted again with fresh Tris buffer to obtain an absorbance (660 nm) of 1.5 on the last resuspension. Cell suspensions were subsequently dispensed into 1.0 ml aliquots and subjected to four cycles of freeze/thaws using dry ice/acetone and 37° C. water baths. The resulting preparation was frozen at about −20° C. until needed.

Preparation of Anti- Treponema Antibodies

A generalized immune response to oral Treponema was generated in six week old female BALB/c mice by immunizing via peritoneal or tail vein injection using 0.1 ml of the above Treponema antigen (33520). Freund's adjuvant was mixed 1:1 with the antigen preparation in order to boost the animal's immune response. The mice were immunized at weekly intervals for three weeks. Three or four days before the cell fusion procedure, the mice were given a 0.1 ml booster immunization of the antigen via tail-vein injection.

Fusion Protocol for Formation of Murine Hybridomas

Initially, a nonsecreting mouse myeloma Sp2.0-Ag14 was cloned in RPMI tissue culture medium (as described in the Journal of the American Medical Association, Vol. 199 p519–524, 1966) containing 0.002% 8-azaguanine. The healthiest clones, i.e. those manifesting strongest growth were then selected for use in the cell fusions to form hybridomas. The fusion promoter used was polyethylene glycol (PEG), although other conventional agents such as Sendai virus may be used to facilitate fusing. The optimum level of polyethylene glycol (PEG) 1500 for formation of the hybridomas was determined by performing cell fusions using non-secreting myeloma Sp2.0-Ag14 cells with spleen cells of six week old female BALB/c mice, at various PEG concentrations. The optimum PEG range is about 40 to about 50% by volume.

Approximately $1 \times 10^7$ myeloma cells and about $5 \times 10^7$ spleen cells from immunized mice were combined, centrifuged and added to a sterile 0.2 ml of polyethylene glycol (PEG) medium comprising polyethylene glycol 1500 (50% by volume), dimethysulfoxide (2.5%), Basal Hybridoma Medium (47.5%) adjusted to pH 7.6 with 0.1N NaOH and maintained for several minutes. The Basal Hybridoma Medium formulation was RPMI 1640 (Gibco Catalogue No. 430-1800) supplemented with 0.25% D-glucose and 25 mM HEPES buffer (N-2-hydroxyethylpiperazine-N'-2-ethanesulfonic acid). The cells were then centrifuged ($400 \times g$) again for about 3 to 6 minutes. Generally, the longer the centrifugation, the more hybrids obtained. A limitation on time is necessary, however, due to the toxic effect of PEG on the cells. The medium was then diluted with the Basal Hybridoma media formulation and then 5ml of the Basal Hybridoma Medium formulation plus 20% fetal bovine serum (FBS) was added. The cells were centrifuged once again, resuspended in 50 ml of hypoxanthine-aminopterin-thymidine (HAT) selective medium and incubated at about 37° C. at 5% $CO_2$ for about 5 to 7 days. Subsequently, each culture was monitored daily and old medium was replaced with fresh medium as cultures began to become slightly acidic. Clones generally become macroscopically present within 2-3 weeks of fusion. Once the clones were visible and the media had become orange-yellow in color, the supernatants were collected and assayed for antibody production using enzyme-linked immuno assay (ELISA) techniques. A conventional sandwich antibody assay, wherein the antigen is coated onto the microtitre plate, was employed. In order to determine accurately the presence of Treponema spirochetes in an immunoassay, the monoclonal antibody must exhibit little or no cross-reactivity with other organisms (antigens).

Assay Procedures for Cross-Reactivity of Various Antigens

Each antigen was tested for reactivity with the inventive monoclonal antibody as per the following procedures.

Approximately 0.1 ml of one to two serial dilutions of 100 micrograms per milliliter of antigen was coated onto a 96 well microtiter plate and the well openings were sealed with plastic. The microtiter plate was then incubated overnight at 4° C. Each well was then washed three times with deionized water and 0.3 ml of 0.1M of Tris buffer, pH 7.2, containing 1% bovine serum albumin (BSA). The microtiter plate was then incubated at room temperature for 1 hour and the wells were again washed three times with deionized water.

At this point, 0.1 ml of monoclonal antibody (culture supernatant) was added to each well and the wells were again sealed with plastic and incubated at 37° C. for 1 hour. The wells were then washed three times with deionized water. In place of deionized water, it is possible to use phosphate buffered saline with BSA or Tween-20 to achieve the same results. About 0.1 ml of goat anti-mouse IgG and IgM-peroxidase conjugate was then added to the wells. The concentration of the conjugate was about 1 to 2,000 to about 1 to 5,000. The wells were than incubated for 1 hour at 37° C., washed three times with deionized water and about 0.1 ml of 0.01% tetramethyl benzidine and 0.005% hydrogen peroxide in a 0.1M citrate/acetate buffer solution, pH 6.0, was added to each well.

As a final stage, 0.05 ml of 2N $H_2SO_4$ was added to the wells and their absorbance was determined by spectrophotometer (450 nm).

The antigens tested are listed below in Table I, along with the indication of reactivity. A plus sign ("+") indicates reactivity and a minus sign ("−") indicates no measurable reactivity. As is evident from the table, hybridomal cell-line ATCC 33520/10 produces monoclonal antibodies which are specific in reactivity to Treponema denticola ATCC 33520. However, as the table also indicates, no measurable reactivity was evident between the inventive monoclonal antibody and the various other antigens (microorganisms) listed.

This specificity indicates the usefulness of the inventive cell line in developing a diagnostic test for Treponema denticola ATCC 33520.

TABLE I

| Microorganism (antigen) | Specificity/Reactivity Cell-line (inventive) 33520/10 |
|---|---|
| T. denticola ATCC #33520 | + |
| T. denticola ATCC #33521 | − |
| T. denticola JD-1 | − |
| T. species 10-A ATCC #43242 | − |
| T. pectinovorum P5 | − |
| T. vincentii N9 | − |
| Actinomyces viscosus | − |
| Bacteroides asaccharolyticus | − |
| Bacteroides gingivalis | − |
| Bacteroides intermedius | − |
| Fusobacterium nucleatum | − |
| Streptococcus pyogenes | − |
| *T. denticola Ichelson | − |

TABLE I-continued

| Microorganism (antigen) | Specificity/Reactivity Cell-line (inventive) 33520/10 |
|---|---|
| *T. denticola D39DP1 | — |
| *T. denticola N39 | — |
| *T. denticola FM | — |
| *T. denticola Ambigua | — |
| *T. denticola TRRD | — |
| *T. denticola IPP | — |
| *T. denticola T32A | — |
| *T. denticola ST10 | — |
| *T. denticola TD2 | — |
| *T. denticola N9 | — |
| *T. socranskii (subspecies buccale D-2B-8) | — |
| *T. denticola D65BR1 | — |
| *T. scoliodontum MNII | — |
| *T. socranskii (subspecies socranskii D-56-B-RIII6) | — |
| *T. socranskii (subspecies paredis D-28-C-3) | — |

*Source, Virginia Polytechnic Institute and State University

We claim:

1. A hybridoma cell-line capable of producing antibody IgG$_3$ to Treponema denticola TCC 33520, wherein the cell line is formed by fusing a nonsecreting mouse myeloma cell with a spleen cell from a mouse immunized with cell fragments of the spirochete Treponema denticola ATCC 33520.

2. The cell-line of claim 1 wherein the strain of the immunized mouse is BALB/c.

3. The cell-line of claim 1 wherein the myeloma cell is Sp2.0-Ag14.

4. The monoclonal antibody of claim 1 having substantially no cross-reactivity with the following microorganisms:

Treponema denticola ATCC #33521
Treponema denticola JD-1
Treponema denticola 10-A ATCC #43242
Treponema pectinovorum P5
Treponema vincentii N9
Actinomyces viscosus
Bacteroides asaccharolyticus
Bacteroides gingivalis
Bacteroides intermedius
Fusobacterium nucleatum
Streptococcus pyogenes
Treponema denticola Ichelson
Treponema denticola D39DP1
Treponema denticola N39
Treponema denticola FM
Treponema denticola Ambigua
Treponema denticola TRRD
Treponema denticola IPP
Treponema denticola T32A
Treponema denticola ST10
Treponema denticola TD2
Treponema denticola N9
Treponema (subspecies buccale D-2B-8)
Treponema denticola D65BR1
Treponema scoliodontum MN11
Treponema socranskii (subspecies socranskii D-56-B-RIII6)
Treponema socranskii (subspecies paredis D-28-C-3)

5. A monoclonal antibody reactive to Treponema species Treponema denticola ATCC 33520, said antibody produced by fusing a nonsecreting mouse myeloma cell Sp2.0-Ag14 with a spleen cell from a Balb/c mouse immunized with cell fragments of the spirochete Treponema denticola ATCC 33520.

* * * * *